United States Patent [19]

Shaw et al.

[11] Patent Number: 5,696,282
[45] Date of Patent: Dec. 9, 1997

[54] PROCESS FOR PRODUCING ORGANOSULFUR COMPOUNDS

[75] Inventors: James E. Shaw, Bartlesville, Okla.; Harry Porter, Overijse, Belgium

[73] Assignee: Phillips Petroleum Company, Bartlesville, Okla.

[21] Appl. No.: 621,925

[22] Filed: Mar. 26, 1996

[51] Int. Cl.$^6$ .................................. C07C 319/16
[52] U.S. Cl. .......................... 560/152; 548/545; 549/253; 558/436; 558/438; 560/145; 560/147; 560/154; 564/154; 564/192; 568/42; 568/43; 568/63
[58] Field of Search .................. 548/545; 549/253; 558/436, 438; 560/145, 147, 152, 154; 564/154, 192; 568/42, 43, 63

[56] References Cited

U.S. PATENT DOCUMENTS

| | | | |
|---|---|---|---|
| 4,052,440 | 10/1977 | Gladstone et al. | 560/154 |
| 4,067,901 | 1/1978 | Gladstone et al. | 560/147 |
| 4,307,225 | 12/1981 | Louthan | 528/279 |
| 5,008,432 | 4/1991 | Roberts | 558/436 |
| 5,057,622 | 10/1991 | Chisholm et al. | 560/152 |
| 5,157,147 | 10/1992 | Chisholm et al. | 560/147 |

OTHER PUBLICATIONS

Reagents for Organic Synthesis (1972), vol. 3, pp. 118–119.
Reagents for Organic Synthesis (1981), vol. 9, p. 178.
Reagents for Organic Synthesis (1982), vol. 10, pp. 155–156.

*Primary Examiner*—Richard L Raymond
*Attorney, Agent, or Firm*—Lucas K. Shay

[57] ABSTRACT

A process comprises contacting, in the presence of a catalyst, hydrogen sulfide or a mercaptan such as, for example, n-dodecyl mercaptan with an $\alpha,\beta$-unsaturated carbonyl or $\alpha,\beta$-unsaturated cyano compound such as, for example, methyl acrylate wherein the catalyst comprises a pyridine derivative such as, for example, 4-(dimethylamino) pyridine or an ion exchange resin such as, for example, "AMBERLYST A-21" to produce a 3-hydrocarbylthio derivative of the $\alpha,\beta$-unsaturated carbonyl or $\alpha,\beta$-unsaturated cyano compound such as, for example, methyl 3-(dodecylthio)propionate.

31 Claims, No Drawings

PROCESS FOR PRODUCING ORGANOSULFUR COMPOUNDS

FIELD OF THE INVENTION

The present invention relates to a process for producing an organosulfur compound such as a 3-mercapto or 3-hydrocarbylthio derivative of carbonyl or cyano compound, especially 3-alkylthio derivatives of α,β-unsaturated esters, α,β-unsaturated ketones, α,β-unsaturated amides, α,β-unsaturated aldehydes, α,β-unsaturated nitriles, and combinations of any two or more thereof.

BACKGROUND OF THE INVENTION

A 3-mercapto or 3-hydrocarbylthio derivative carbonyl or cyano compound such as, for example, methyl 3-(n-dodecylthio)propionate, can be used itself or converted to a free acid form which is generally used as an intermediate for production of antioxidants such as, for example, pentaerythritol tetrakis(n-dodecylthio)propionate. Production of the chemicals from a mercaptan and chloropropionic acid were not very satisfactory because chloropropionic acid is expensive and the reaction is not easy to carry out. Therefore, it would be a significant contribution to the art if a process can be developed which produces the compounds in high yield and high selectivity.

SUMMARY OF THE INVENTION

An object of the present invention is to provide a process for producing an organosulfur compound. Another object of the present invention is to provide a process for producing an organosulfur compound in high yield and high selectivity. Other objects, advantages, or features of the present invention will become more apparent as the invention is more fully disclosed hereinbelow.

According to the present invention, a process which can be used for producing an organosulfur compound such as a 3-mercapto or 3-hydrocarbylthio derivative of carbonyl or cyano compound is provided. The process comprises, consists essentially of, or consists of, contacting a sulfhydryl compound having the formula of $R(SH)_n$, in the presence of a catalyst, with an α,β-unsaturated carbonyl or α,β-unsaturated cyano compound wherein R is selected from the group consisting of hydrogen, alkyl radicals, alkenyl radicals, aryl radicals, alkaryl radicals, aralkyl radicals, and combinations of any two or more thereof; the catalyst can comprise, consists essentially of, or consists of pyridine derivative, ion exchange resin, or combinations of any two or more thereof; and n is at least 1, preferably $1 \leq n \leq 3$.

DETAILED DESCRIPTION OF THE INVENTION

According to the present invention, an organosulfur compound such as a 3-mercapto or 3-hydrocarbylthio derivative of an α,β-unsaturated carbonyl or cyano compound is produced from a sulfhydryl compound and an α,β-unsaturated carbonyl or cyano compound. The presently preferred organosulfur compounds have a general formula selected from the group consisting of RS—C(R")$_2$—CH(R")—W, W—C(R")(SR)—CH(R")—W,

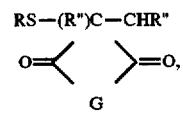

and combinations of any two or more thereof; wherein each R and R" can be the same or different hydrocarbyl radicals or hydrogen and is each independently selected from the group consisting of hydrogen, alkyl radicals, alkenyl radicals, aryl radicals, alkaryl radicals, aralkyl radicals, and combinations of any two or more thereof; W is selected from the group consisting of COOR', C≡N, C(O)R'"—OH, C(O)NR$_2$, C(O)R, and combinations of any two or more thereof; R' can be the same as or different from R and is selected from the group consisting of alkyl radicals, alkenyl radicals, aryl radicals, alkaryl radicals, aralkyl radicals, and combinations of any two or more thereof; R'" is an alkylene radical; and G is O or NR. Each radical can have 1 to about 30, preferably to about 25, and most preferably to 20 carbon atoms. The radicals can be linear, branched, cyclic, substituted, or combinations of any two or more thereof. The presently preferred organosulfur compounds have the formula of RS—C(R")$_2$—CH(R")—W as disclosed below.

Examples of organosulfur compounds include, but are not limited to, 3-alkylthio derivatives of α,β-unsaturated esters, 3-alkylthio derivatives of α,β-unsaturated ketones, 3-alkylthio derivatives of α,β-unsaturated amides, 3-alkylthio derivatives of α,β-unsaturated nitriles, 3-alkylthio derivatives of α,β-unsaturated aldehydes, and combinations of any two or more thereof. Specific examples of organosulfur compounds include, but are not limited to, methyl 3-mercaptopropionate, benzyl 3-mercaptopropionate, methyl 3-(dodecylthio)propionate, ethyl 3-(dodecylthio)propionate, benzyl 3-(dodecylthio)propionate, tolyl 3-(dodecylthio)propionate, methyl 3-(t-dodecylthio)propionate, methyl 3-(nonylthiol)propionate, methyl 3-(t-butylthio)propionate, methyl 3-(cyclohexylthio)propionate, methyl 3-(hexylthio)propionate, methyl 3-(dodecylthio)-2-methylpropionate, methyl 3-(benzylthio)propionate, ethyl 3-(benzylthio)propionate, ethyl 3-(t-dodecylthio)propionate, 3-(ethylthio)butanal, 3-(dodecylthio)propionaldehyde, methyl 3-(dodecylthio)propanenitrile, 3-(ethylthio)propanenitrile, 4-phenyl-4-(ethylthio)butan-2-one, and combinations of any two or more thereof. The presently preferred organosulfur compound is methyl 3-(dodecylthio)propionate for it can be hydrolyzed to a free acid form 3-(dodecylthio)propionic acid, which can be used as an intermediate for producing an antioxidant.

As disclosed above, the organosulfur compounds of the invention are produced by contacting a sulfhydryl compound such as hydrogen sulfide or a mercaptan with an α,β-unsaturated carbonyl or cyano compound, in the presence of a pyridine derivative. The sulfhydryl compound useful in the process of the present invention has the formula of $R(SH)_n$ wherein R and n are the same as those disclosed above. Examples of suitable sulfhydryl compounds include, but are not limited to, hydrogen sulfide, methyl mercaptan, ethyl mercaptan, propyl mercaptan, isopropyl mercaptan, butyl mercaptan, isobutyl mercaptan, t-butyl mercaptan, amyl mercaptan, hexyl mercaptan, cyclohexyl mercaptan, octyl mercaptan, nonyl mercaptan, decyl mercaptan, dodecyl mercaptan, t-dodecyl mercaptan, benzyl mercaptan, thiophenol, tolyl mercaptan, 1,2-ethanedithiol, 1,2-methanedithiol, 1,2,3-propanetrithiol, and combinations of any two or more thereof. These mercaptans are believed commercially available. The presently preferred mercaptan is dodecyl mercaptan because it can be used to produce the methyl 3-(dodecylthio)propionate disclosed above.

The α,β-unsaturated carbonyl or cyano compounds have the formula of R"₂C=C(R")—W, W—C(R")=C(R")—W,

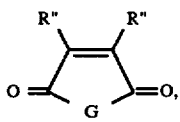

and combinations of any two or more thereof in which W, G, and R" are the same as those disclosed above. Examples of suitable α,β-unsaturated carbonyl or cyano compounds include, but are not limited to, methyl acrylate, methyl methacrylate, acrolein, methacrolein, crotonaldehyde, cinnamaldehyde, benzalacetone (4-phenyl-3-buten-2-one), mesityl oxide (4-methyl-3-penten-2-one), dimethyl maleate, methyl vinyl ketone, dimethyl fumarate, maleic anhydride, maleic anhydride, ethyl crotonate, cinnamic acid, methyl acrylonitrile, acrylamide, methacrylamide, N,N-dimethyl acrylamide, maleimide, and combinations of any two or more thereof. These compounds are believed commercially available. The presently preferred α,β-unsaturated carbonyl compound is methyl acrylate for it is useful for the production of the above-disclosed methyl 3-(dodecylthio) propionate.

Generally any pyridine derivatives can be used so long as the pyridine derivatives can effectively catalyze the production of a 3-mercapto or 3-hydrocarbylthio derivative of α,β-unsaturated carbonyl or cyano compounds. The presently preferred pyridine derivative has the formula of

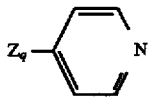

in which each Z can be the same or different and is a substituent selected from the group consisting of R', R₂N, RO, R'S, W, X, and combinations of any two or more thereof and q is a whole number of 1 to 5 wherein R, R', and are the same as those disclosed above and X is a halogen. Each Z can be at any available position of the pyridine ring. Examples of suitable pyridine derivatives include, but are not limited to, 4-(dimethylamino)pyridine, 4-piperidinopyridine, 2,3,4,6-tetramethylpyridine, 2,3,5-trimethylpyridine, 2-benzylpyridine, 3-chloropyridine, 2-chloro-5-nitropyridine, 2,3-diaminopyridine, 4-methoxypyridine, 3,4-diaminopyridine, 2,6-dimethyl-3-ethylpyridine, 2-hydroxyethylpyridine, 2-(methylthio) pyridine, 2-methylaminopyridine, 3-acetamidopyridine, 2-benzoylpyridine, and combinations of any two or more thereof. These pyridine derivatives are believed commercially available. The presently most preferred pyridine derivative is 4-(dimethylamino)pyridine for it is readily available.

Any ionic resins that can effect the production of the organosulfur compounds disclosed herein can be employed in the present invention. The presently preferred ionic resin can comprise, or consist essentially of, or consist of an anion ion exchange resin. Generally, an ionic resin is a polymer which separates molecules based on differences in charge. A basic or anion ion exchange resin is useful for electrostatic sorption of substances with negative charge. The active group of an anion ion exchange resin can comprise, for example, a tertiary amine, a polyamine, a quaternary ammonium, tetraalkylammonium hydroxide groups, other amines, or combinations thereof. Generally, the ion exchange resins comprise, consist essentially of, or consist of greater than about 40, preferably 50, and most preferably about 60 weight % of the resin. The resins can also contain a solvent such as, for example, water.

Examples of suitable anion ion exchange resins include, but are not limited to, DEAE (diethylaminoethyl) cellulose, ECTEOLA (epichlorohydrin triethanolamine) cellulose, DEAE sephadex (a dextran), "AMBERLITE" ion exchangers, "DOWEX" ion exchangers, "LEWATIT" ion exchangers, and combinations of any two or more thereof. These ion exchange resins are commercially available and are well known to one skilled in the art. The presently preferred ion exchange resin is a weakly basic anion exchange resin having the tradename of "AMBERLYST A-21".

The amount of the ion exchange resin required is the amount sufficient to effect the production of the organosulfur compounds disclosed herein. Generally the amount can be in the range of from about 0.0001 to about 5, preferably about 0.001 to about 2, and most preferably 0.005 to 0.5 g of resin per g of hydrocarbon-containing fluid to be contacted.

According to the present invention, the molar ratio of sulfhydryl compound to the α,β-unsaturated carbonyl or cyano compound can be any ratio which can effect the production of a 3-mercapto or a 3-hydrocarbylthio carbonyl or cyano compound. Generally the molar ratio of hydrogen sulfide to the α,β-unsaturated carbonyl or cyano compound can be in the range of from about 0.1:1 to about 50:1, preferably about 1:1 to about 20:1, and most preferably 2:1 to 10:1. The molar ratio of a mercaptan to the α,β-unsaturated carbonyl or cyano compound can be in the range of from about 0.01:1 to about 1:1, preferably about 0.1:1 to about 5:1, and most preferably 0.25:1 to 2:1. The quantity of pyridine derivative can be any quantity that can effectively catalyze the contacting of sulfhydryl compound and an α,β-unsaturated carbonyl or cyano compound for the production of an organosulfur compound of the invention. Generally, the molar ratio of pyridine derivative to hydrogen sulfide or mercaptan can be in the range of from about 0.001:1 to about 0.5:1, preferably about 0.005:1 to about 0.2:1, and most preferably 0.01:1 to 0.1:1.

The process of the invention can also be carried out in the presence of a solvent if a solvent can facilitate the contacting of the sulfhydryl compound with an α,β-unsaturated carbonyl or cyano compound. Such a solvent can be a hydrocarbon, an ether, a ketone, an alcohol, or combinations of any two or more thereof. If a solvent is employed, the quantity of the solvent can be any quantity that can facilitate the contacting of the sulfhydryl compound with an α,β-unsaturated carbonyl or cyano compound. The molar ratio of a solvent to the sulfhydryl compound can be in the range of from about 0.01:1 to about 100:1.

According to the present invention, the contacting can be carried out under any condition so long as the condition is sufficient to effect the production of a 3-mercapto or a 3-hydrocarbylthio compound of α,β-unsaturated carbonyl or cyano compound. Generally, such a condition can include a temperature in the range of from about 40° C. to about 200° C., preferably about 60° C. to about 150° C., and most preferably 75° C. to 120° C.; a pressure in the range of from about 0.5 atmosphere (atm) to about 50 atm, preferably about 0.8 atm to about 15 atm, and most preferably 0.9 atm to 10 atm; and a contacting time of from about 1 to about 25 hours, preferably about 1 to about 20 hours, and most preferably 1 to 15 hours.

Upon completion of the contacting of hydrogen sulfide or mercaptan with an α,β-unsaturated carbonyl or cyano compound, the organosulfur compound produced can be used as is, or further processed such as, for example, hydrolyzed to its free acid form, or separated and recovered from the contacting medium. Any means known to one skilled in the art such as, for example, evaporation, can be used for further process, separation, or recovery of the organosulfur compounds. Because it is not in the scope of the present invention, description of which is omitted herein for the interest of brevity.

The process of the present invention can be carried out as a batch process, a semicontinous process, or a continuous process such as continuously passing the sulfhydryl compound and the $\alpha,\beta$-unsaturated carbonyl or cyano compound through any suitable reactor or column packed with an ion exchange resin under the conditions disclosed above. Any suitable feed rate can be employed. For example, the hourly space velocity (HSV) of the sulfhydryl compound and the $\alpha,\beta$-unsaturated carbonyl or cyano compound can be about 0.001 to about 100, preferably about 0.005 to about 50, and most preferably 0.01 to 10 grams (e.g., ml) fluid per gram of ion exchange resin per hour.

The following non-limiting examples are provided to illustrate the process of the invention.

EXAMPLE I

This example illustrates the process of the present invention.

To a 3 liter, 3-necked flask equipped with a thermowell, magnetic stirring bar, pressure equalizing addition funnel, and condenser with $N_2$ inlet on top was added 8.2 g (0.067 mole) of 4-(dimethylamino)pyridine and 538 g (2.66 moles) of n-dodecyl mercaptan to form a mixture. The mixture was heated with stirring to 40°–50° C. to become solution and then 758 g (8.81 moles) of methyl acrylate was added, from the addition funnel over 5–10 minutes, to the solution. No noticeable exothermic reaction occurred. The reaction mixture was then heated to 92° C. (reflux) for 11 hours. The reflux temperature at the end of this time was slightly higher (93°–94° C.). The reaction time was determined by taking samples periodically for GC analysis (20 in.×⅛ in. 2% OV-101 packed column, column temperature 50° C. initially and then 15° C./min., injection port 225° C., FID detector) until the n-dodecyl mercaptan content was approximately 0.1%. The reaction mixture was cooled to room temperature and transferred to a flask for evaporation on a rotary evaporator at approximately 20 torr and 95° C. for 1.5–2 hours. This removed excess methyl acrylate. The weight of residual liquid was 808 g. The residual liquid was then sparged with $N_2$ (gas dispersion tube, 2 SCFH $N_2$) for 1.5–2 hours at 75°–80° C. to remove more methyl acrylate. The weight of yellow-orange liquid after sparging was 799 g. GC analysis of the liquid showed that it consisted of 96.8% methyl 3-(n-dodecylthio)propionate, 0.4% of dodecyl isomers of the main product, 1.2% of the main product reacted with 1 additional methyl acrylate molecule, 0.7% of the main product reacted with 2 additional methyl acrylate, 0.4% of the main product reacted with 3 additional methyl acrylate, 0.1% n-dodecyl mercaptan, 0.1% methyl acrylate, and 0.3% other lights. The 799 g of liquid represented a 103% yield if the contribution of catalyst (8.2 g) is subtracted. The higher than theoretical yield was probably the result of polymer formation from methyl acrylate which was too heavy for GC analysis. The actual weight % of methyl 3-(n-dodecylthio) propionate would be about 94% if these factors were taken into account.

The above reaction was repeated. The final liquid product had a slightly different composition. It contained 92.8% of methyl 3-(n-dodecylthio)propionate, 0.4% of dodecyl isomers of the main product, 2.9% of the main product reacted with 1 additional methyl acrylate molecule, 1.6% of the main product reacted with 2 additional methyl acrylate, 0.9% of the main product reacted with 3 additional methyl acrylate, 0.4% of the main product reacted with 4 additional methyl acrylate, 0.3% other heavies, 0.1% n-dodecyl mercaptan, 0.1% methyl acrylate, and 0.5% other lights.

On the GC, methyl 3-(n-dodecylthio)propionate appeared to decompose slightly to starting materials at high injection port temperatures. Although an injection port temperature of 225° C. was used so all heavies would be eluted, an injection temperature of 175° C. was used to measure remaining n-dodecyl mercaptan and methyl acrylate.

EXAMPLE II

This example further illustrates the process of the present invention.

To a 500 ml, 3-necked flask equipped with thermowell, magnetic stirring bar, pressure equalizing addition funnel, and condenser with $N_2$ inlet on top was added 0.78 g (0.0064 mole) of 4-(dimethylamino)pyridine, 67.2 g (0.332 mole) of n-dodecyl mercaptan, and 94.8% (1.10 moles) of methyl acrylate. The mixture was heated to reflux (at about 92° C.) with stirring. Samples were taken after 0.5 hour and then after each hours for GC analysis (see Example I). GC results showed the reaction mixture consisted of the following components at the reaction time listed.

| Reaction Time (hours) | % components by GC | | | |
| --- | --- | --- | --- | --- |
| | Desired Product[a] | Dodecyl Mercaptan | Methyl Acrylate | Heavies[b] |
| 0.5 | 40.4 | 31.0 | 21.7 | 2.2 |
| 1.0 | 51.9 | 23.2 | 21.2 | 3.4 |
| 2.0 | 64.8 | 11.6 | 19.7 | 3.8 |
| 3.0 | 66.7 | 9.1 | 19.6 | 4.2 |
| 4.0 | 67.7 | 7.7 | 19.6 | 4.6 |
| 5.0 | 70.6 | 5.7 | 18.6 | 4.7 |
| 6.0 | 71.1 | 4.5 | 18.5 | 5.6 |

[a]Desired product is methyl 3-(n-dodecylthio)propionate.
[b]Heavier than desired product.

EXAMPLE III

This is a comparative example illustrating runs using a different catalyst.

The reaction was carried out the same way as in Example II except that triethylamine (0.73 g, 0.0072 mole) was used as catalyst instead of 4-(dimethylamino)pyridine. GC results showed the reaction mixture consisted of the following at the reaction times listed.

| Reaction Time (hours) | % Components by GC | | | |
| --- | --- | --- | --- | --- |
| | Desired Product | Dodecyl Mercaptan | Methyl Acrylate | Heavies |
| 0.5 | 5.8 | 48.9 | 34.4 | 9.8 |
| 1.0 | 10.2 | 41.1 | 33.2 | 14.0 |
| 2.0 | 20.2 | 32.1 | 29.2 | 17.3 |
| 3.0 | 43.0 | 11.2 | 24.1 | 20.5 |
| 4.0 | 53.8 | 2.1 | 21.4 | 21.6 |
| 5.0 | 55.7 | 1.1 | 18.9 | 23.2 |
| 6.0 | 55.2 | 0.8 | 16.7 | 26.4 |

The results shown in EXAMPLES I–III demonstrate that reaction using 4-(dimethylamino)pyridine produced methyl 3-(n-dodecylthio)propionate much more rapidly than that using triethylamine. More importantly, the reaction using 4-(dimethylamino)pyridine produced much less heavies (products heavier than the desired product) than that using triethylamine.

EXAMPLE IV

This example shows runs carried out with acrylic acid instead of methyl acrylate.

One run was carried out in a 500 ml flask with thermowell, magnetic stir bar, condenser with $N_2$ inlet on top, pressure equalizing addition funnel. To this flask, it was added 0.50 g of 4-(dimethylamino)pyridine and 105 g of n-dodecyl mercaptan to form a mixture. The mixture was heated to 70° C. and thereafter, using a, addition funnel, 37.4 g of acrylic acid was added to the flask over 15–20 minutes. No noticeable exothermic reaction was observed. The mixture was then heated to 80° C., 90° C., eventually 100° C. and the content of the flask was sampled at various times for GC analysis. The GC results showed that little desired product was produced.

EXAMPLE V

This example also is a comparative example illustrating that an unsubstituted pyridine is not a satisfactory catalyst for the production of a 3-hydrocarbylthio compound.

The run was carried out using the same procedure as described in EXAMPLE II with the exception that pyridine was used in place of 4-(dimethylamino)pyridine.

As shown in the following table, the results were poor. There was slow formation of desired product and a lot of heavies were formed instead. The results demonstrate that 4-(dimethylamino)pyridine was far superior to pyridine as catalyst for the process of the present invention.

| Reaction Time (hours) | % Components by GC | | | |
|---|---|---|---|---|
| | Desired Product | Dodecyl Mercaptan | Methyl Acrylate | Heavies |
| 0.5 | 10.7 | 41.9 | 18.0 | 28.9 |
| 1.0 | 10.4 | 40.3 | 18.3 | 29.7 |
| 2.0 | 12.1 | 36.4 | 19.9 | 30.1 |
| 3.0 | 13.2 | 33.8 | 15.5 | 36.1 |

EXAMPLE VI

This example illustrates that the process of the invention can be catalyzed by an ion exchange resin.

To a 500 ml, 3-necked flask equipped with thermowell, magnetic stir bar, pressure equalizing addition funnel, and condenser with $N_2$ inlet on top was added 6.0 g of Amberlyst 21 (purchased from Rohm and Haas, Philadelphia, Pa.) and 101 g of n-dodecyl mercaptan. The setup was flushed with $N_2$ and the mixture was heated to 80° C. with stirring. Then by addition funnel was added 86 g of methyl acrylate at a rate to keep the exothermic reaction under control. The addition was carried out in 20 to 30 minutes. The reaction mixture was then heated with stirring for 5 hours at 80°–85° C. After cooling to room temperature, the reaction mixture was filtered to remove Amberlyst 21. The filtrate was evaporated on a rotary evaporator under about 20 torr at 95° C. for 1 hour to remove excess methyl acrylate. The last traces of methyl acrylate were removed by sparging the liquid product with $N_2$ at 80° C. for 1.5 hours. The colorless liquid product weighed 138 g (96% yield). GC analysis showed the product consisted of 97.6% of methyl 3-(n-dodecylthio)propionate, 0.5% of dodecyl isomers of the main product, 1.2% of the main product reacted with one additional methyl acrylate molecule, 0.4% of the main product reacted with 2 additional methyl acrylate molecules, 0.1% of n-dodecyl mercaptan, 0.1% methyl acrylate, and 0.1% other lights. These results demonstrate that an ion exchange resin can also be used in the invention process.

The results shown in the above example clearly demonstrate that the present invention is well adapted to carry out the objects and attain the end and advantages mentioned as well as those inherent therein. While modifications may be made by those skilled in the art, such modifications are encompassed within the spirit of the present invention as defined by the disclosure and the claims.

That which is claimed:

1. A process comprising contacting a sulfhydryl compound having the formula of $R(SH)_n$, in the presence of a catalyst, with an $\alpha,\beta$-unsaturated carbonyl or $\alpha,\beta$-unsaturated cyano compound under a condition effective to produce an organosulfur compound selected from the group consisting of 3-mercapto derivative of $\alpha,\beta$-unsaturated carbonyl compounds, 3-mercapto derivative of $\alpha,\beta$-unsaturated cyano compounds, 3-hydrocarbylthio derivative of $\alpha,\beta$-unsaturated carbonyl compounds, 3-hydrocarbylthio derivative of $\alpha,\beta$-unsaturated cyano compounds, and combinations of any two or more thereof wherein R is selected from the group consisting of alkyl radicals, alkenyl radicals, aryl radicals, alkaryl radicals, aralkyl radicals, and combinations thereof; $1 \leq n \leq 3$; said $\alpha,\beta$-unsaturated carbonyl compound is not acrylic acid; and said catalyst is selected from the group consisting of pyridine derivatives, anionic ion exchange resins, and combinations of any two or more thereof.

2. A process according to claim 1 wherein said organosulfur compound has the formula selected from the group of RS—C(R")$_2$—CH(R")—W, W—C(R")(SR)—CH(R")—W,

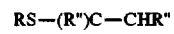

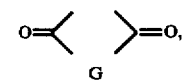

and combinations of any two or more thereof wherein each R and R" are independently selected from the group consisting of hydrogen, alkyl radicals, alkenyl radicals, aryl radicals, alkaryl radicals, aralkyl radicals, and combinations thereof; W is selected from the group consisting of COOR', C≡N, C(O)R'''—OH, C(O)NR$_2$, C(O)R, and combinations of any two or more thereof; R' is selected from the group consisting of alkyl radicals, alkenyl radicals, aryl radicals, alkaryl radicals, aralkyl radicals, and combinations of any two or more thereof; R''' is an alkylene radical; and G is O or NR.

3. A process according to claim 2 wherein W is COOR'.

4. A process according to claim 3 wherein R and R' are each independently an alkyl radical.

5. A process according to claim 3 wherein R is n-dodecyl radical.

6. A process according to claim 3 wherein R' is methyl radical.

7. A process according to claim 2 wherein each R" is hydrogen.

8. A process according to claim 3 wherein each R" is hydrogen.

9. A process according to claim 2 wherein said organosulfur compound is selected from the group consisting of methyl 3-mercaptopropionate, benzyl 3-mercaptopropionate, methyl 3-(dodecylthio)propionate, ethyl 3-(dodecylthio)propionate, benzyl 3-(dodecylthio) propionate, tolyl 3-(dodecylthio)propionate, methyl 3-(t-dodecylthio)propionate, methyl 3-(nonylthiol)propionate, methyl 3-(t-butylthio)propionate, methyl 3-(cyclohexylthiol)propionate, methyl 3-(hexylthio) propionate, methyl 3-(dodecylthio)-2-methylpropionate, methyl 3-(benzylthio)propionate, ethyl 3-(benzylthio) propionate, ethyl 3-(t-dodecylthio)propionate, and combinations of any two or more thereof.

10. A process according to claim 2 wherein said organosulfur compound is methyl 3-(n-dodecylthio)propionate.

11. A process according to claim 1 wherein said catalyst is a weakly basic anion exchange resin.

12. A process according to claim 1 wherein said catalyst is a pyridine derivative.

13. A process according to claim 12 wherein said pyridine derivative has the formula of

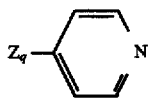

wherein each Z is independently selected from the group consisting of R', $R_2N$, OR, SR', W, X, and combinations of any two or more thereof wherein each R is independently selected from the group consisting of hydrogen, alkyl radicals, alkenyl radicals, aryl radicals, alkaryl radicals, aralkyl radicals, and combinations thereof; each R' is independently selected from the group consisting of alkyl radicals, alkenyl radicals, aryl radicals, alkaryl radicals, aralkyl radicals, and combinations thereof; W is selected from the group consisting of COOR', C≡N, C(O)R'''—OH, $C(O)NR_2$, C(O)R, and combinations of any two or more thereof; X is a halogen; q is a whole number from 1 to 5; R''' is an alkylene radical; and $Z_q$ can be at any available positions of the pyridine ring.

14. A process according to claim 13 wherein said pyridine derivative is selected from the group consisting of 4-(dimethylamino)pyridine, 4-piperidinopyridine, 2,3,4,6-tetramethylpyridine, 2,3,5-trimethylpyridine, 2-benzylpyridine, 3-chloropyridine, 2-chloro-5-nitropyridine, 2,3-diaminopyridine, 4-methoxypyridine, 3,4-diaminopyridine, 2,6-dimethyl-3-ethylpyridine, 2-hydroxyethylpyridine, 2-(methylthio)pyridine, 2-methylaminopyridine, 3-acetamidopyridine, 2-benzoylpyridine, and combinations of any two or more thereof.

15. A process according to claim 13 wherein Z is $R_2N$.

16. A process according to claim 15 wherein each R is methyl radical.

17. A process according to claim 16 wherein q is 1.

18. A process according to claim 17 wherein said catalyst is 4-(dimethylamino)pyridine.

19. A process according to claim 2 wherein said sulfhydryl compound is selected from the group consisting of hydrogen sulfide, methyl mercaptan, ethyl mercaptan, propyl mercaptan, isopropyl mercaptan, butyl mercaptan, isobutyl mercaptan, t-butyl mercaptan, amyl mercaptan, hexyl mercaptan, cyclohexyl mercaptan, octyl mercaptan, nonyl mercaptan, decyl mercaptan, dodecyl mercaptan, t-dodecyl mercaptan, benzyl mercaptan, thiophenol, tolyl mercaptan, 1,2-ethanedithiol, 1,2-methanedithiol, 1,2,3-propanetrithiol, and combinations of any two or more thereof.

20. A process according to claim 2 wherein said sulfhydryl compound is n-dodecylmercaptan.

21. A process according to claim 2 wherein said α,β-unsaturated carbonyl or α,β-unsaturated cyano compound has the formula of $R''_2C=C(R'')$—W, W—(R'')=C(R'')—W,

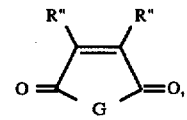

and combinations of any two or more thereof wherein each R'' is independently selected from the group consisting of hydrogen, alkyl radicals, alkenyl radicals, aryl radicals, alkaryl radicals, aralkyl radicals, and combinations of any two thereof; W is selected from the group consisting of COOR', C≡N, C(O)R'''—OH, $C(O)NR_2$, C(O)R, and combinations of any two or more thereof; each R is independently selected from the group consisting of alkyl radicals, alkenyl radicals, aryl radicals, alkaryl radicals, aralkyl radicals, and combinations of any two thereof; R' is selected from the group consisting of alkyl radicals, alkenyl radicals, aryl radicals, alkaryl radicals, aralkyl radicals, and combinations of any two or more thereof; R''' is an alkylene radical; and G is O or NR.

22. A process according to claim 21 wherein W is COOR'.

23. A process according to claim 22 wherein R' is methyl radical.

24. A process according to claim 21 wherein said α,β-unsaturated carbonyl or cyano compound is selected from the group consisting of methyl acrylate, methyl methacrylate, acrolein, methacrolein, crotonaldehyde, cinnamaldehyde, benzalacetone (4-phenyl-3-buten-2-one), mesityl oxide (4-methyl-3-penten-2-one), dimethyl maleate, methyl vinyl ketone, dimethyl fumarate, maleic anhydride, maleic anhydride, ethyl crotonate, cinnamic acid, methyl acrylonitrile, acrylamide, methacrylamide, N,N-dimethyl acrylamide, maleimide, and combinations of any two or more thereof.

25. A process according to claim 24 wherein said α,β-unsaturated compound is methyl acrylate.

26. A process comprising contacting a sulfhydryl compound having the formula of $R(SH)_n$, in the presence of a catalyst, with an α,β-unsaturated carbonyl or α,β-unsaturated cyano compound under a condition effective to produce an orangosulfur compound wherein said organosulfur compound has the formula selected from the group of RS—$C(R'')_2$—CH(R'')—W, W—C(R'')(SR)—CH(R'')—W,

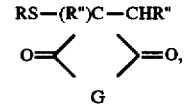

and combinations of any two or more thereof wherein each R and R'' are independently selected from the group consisting of hydrogen, alkyl radicals, alkenyl radicals, aryl radicals, alkaryl radicals, aralkyl radicals, and combinations thereof R' is selected from the group consisting of alkyl radicals, alkenyl radicals, aryl radicals, alkaryl radicals, aralkyl radicals, and combinations thereof; W is selected from the group consisting of COOR', C≡N, C(O)R'''—OH, $C(O)NR_2$, C(O)R, and combinations of any two or more thereof; R' is selected from the group consisting of alkyl radicals, alkenyl radicals, aryl radicals, alkaryl radicals, aralkyl radicals, and combinations of any two or more thereof; R''' is an alkylene radical; $1 \leq n \leq 3$; and G is O or NR;

catalyst is selected from the group consisting of pyridine derivatives, anionic ion exchange resins, and combinations of two or more thereof wherein said pyridine derivative has the formula of

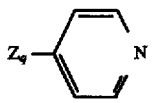

wherein each Z is independently selected from the group consisting of R', R₂N, OR, SR', W, X, and combinations of any two or more thereof wherein X is a halogen; q is a whole number from 1 to 5; and $Z_q$ can be at any available positions of the pyridine ring; and α,β-unsaturated carbonyl or α,β-unsaturated cyano compound has the formula of R"₂C=C(R")—W, W—(R")=C(R")—W,

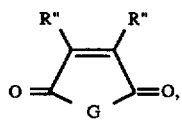

and combinations of any two or more thereof.

27. A process according to claim 26 wherein said organosulfur compound is selected from the group consisting of methyl 3-mercaptopropionate, benzyl 3-mercaptopropionate, methyl 3-(dodecylthio) propionate, ethyl 3-(dodecylthio)propionate, benzyl, 3-(dodecylthio)propionate, tolyl 3-(dodecylthio) propionate, methyl 3-(t-dodecylthio)propionate, methyl 3-(nonylthiol)propionate, methyl 3-(t-butylthio)propionate, methyl 3-(cyclohexylthiol) propionate, methyl 3-(hexylthio)propionate, methyl 3-(dodecylthio)-2-methylpropionate, methyl 3-(benzylthio)propionate, ethyl 3-(benzylthio) propionate, ethyl 3-(t-dodecylthio)propionate, and combinations of any two or more thereof;

pyridine derivative is selected from the group consisting of 4-(dimethylamino)pyridine, 4-piperidinopyridine, 2,3,4,6-tetramethylpyridine, 2,3,5-trimethylpyridine, 2-benzylpyridine, 3-chloropyridine, 2-chloro-5-nitropyridine, 2,3-diaminopyridine, 4-methoxypyridine, 3,4-diaminopyridine, 2,6-dimethyl-3-ethylpyridine, 2-hydroxyethylpyridine, 2-(methylthio)pyridine, 2-methylaminopyridine, 3-acetamidopyridine, 2-benzoylpyridine, and combinations of any two or more thereof; sulfhydryl compound is selected from the group consisting of hydrogen sulfide, methyl mercaptan, ethyl mercaptan, propyl mercaptan, isopropyl mercaptan, butyl mercaptan, isobutyl mercaptan, t-butyl mercaptan, amyl mercaptan, hexyl mercaptan, cyclohexyl mercaptan, octyl mercaptan, nonyl mercaptan, decyl mercaptan, dodecyl mercaptan, t-dodecyl mercaptan, benzyl mercaptan, thiophenol, tolyl mercaptan, 1,2-ethanedithiol, 1,2-methanedithiol, 1,2,3-propanetrithiol, and combinations of any two or more thereof; and α,β-unsaturated carbonyl or α,β-unsaturated cyano compound is selected from the group consisting of methyl acrylate, methyl methacrylate, acrolein, methacrolein, crotonaldehyde, cinnamaldehyde, benzalacetone (4-phenyl-3-buten-2-one), mesityl oxide (4-methyl-3-penten-2-one), dimethyl maleate, methyl vinyl ketone, dimethyl fumarate, maleic anhydride, maleic anhydride, ethyl crotonate, cinnamic acid, methyl acrylonitrile, acrylamide, methacrylamide, N,N-dimethyl acrylamide, maleimide, and combinations of any two or more thereof.

28. A process according to claim 26, wherein said organosulfur compound is methyl 3-(n-dodecylthio)propionate; said catalyst is 4-(dimethylamino)pyridine; said sulfhydryl compound is n-dodecylmercaptan; and said α,β-unsaturated carbonyl compound is methyl acrylate.

29. A process according to claim 26 wherein said organosulfur compound is methyl 3-(n-dodecylthio)propionate; said catalyst is a weakly basic anion exchange resin; said sulfhydryl compound is n-dodecylmercaptan; and said α,β-unsaturated carbonyl compound is methyl acrylate.

30. A process for producing methyl 3-(dodecylthio) propionate comprising contacting dodecyl mercaptan, in the presence of 4-(dimethylamino)pyridine, with methyl acrylate wherein the molar ratio of dodecyl mercaptan to methyl acrylate is in the range of from 0.25:1 to 1:1.

31. A process for producing methyl 3-(dodecylthio) propionate comprising contacting dodecyl mercaptan, in the presence of a weakly basic anion exchange resin, with methyl acrylate wherein the molar ratio of dodecyl mercaptan to methyl acrylate is in the range of from 0.25:1 to 1:1.

* * * * *